(12) United States Patent
Gerberding et al.

(10) Patent No.: US 10,219,924 B2
(45) Date of Patent: Mar. 5, 2019

(54) MULTILAYER STENT

(71) Applicants: STRYKER CORPORATION, Kalamazoo, MI (US); STRYKER NV OPERATIONS LIMITED, Dublin (IE)

(72) Inventors: Brent C. Gerberding, San Jose, CA (US); Ted W. Layman, Park City, UT (US); Clay W. Northrop, Salt Lake City, UT (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 520 days.

(21) Appl. No.: 14/139,815

(22) Filed: Dec. 23, 2013

(65) Prior Publication Data

US 2014/0180397 A1 Jun. 26, 2014

Related U.S. Application Data

(60) Provisional application No. 61/784,798, filed on Mar. 14, 2013, provisional application No. 61/745,913, filed on Dec. 26, 2012.

(51) Int. Cl.
*A61F 2/82* (2013.01)
*A61F 2/88* (2006.01)
(Continued)

(52) U.S. Cl.
CPC .............. *A61F 2/915* (2013.01); *A61F 2/852* (2013.01); *A61F 2/88* (2013.01); *A61F 2/90* (2013.01);
(Continued)

(58) Field of Classification Search
CPC ................ A61F 2/852; A61F 2002/823; A61F 2002/821; A61F 2/82; A61F 2/88; A61F 2/885; A61F 2002/826; A61F 2002/828
See application file for complete search history.

(56) References Cited

U.S. PATENT DOCUMENTS 4,312,353 A 1/1982 Shahbabian
4,921,478 A 5/1990 Solano et al.
(Continued)

FOREIGN PATENT DOCUMENTS

CA 2 821 084 6/2012
EP 1870057 12/2007
(Continued)

OTHER PUBLICATIONS

PCT International Search Report and Written Opinion for PCT/US2005/004494, Applicant Boston Scientific Scimed, Inc., Forms PCT/ISA/210, 220, and 237 dated Jun. 20, 2005 (12 pages).
(Continued)

*Primary Examiner* — Katrina M Stransky
*Assistant Examiner* — Lindsey Bachman
(74) *Attorney, Agent, or Firm* — Vista IP Law Group LLP

(57) ABSTRACT

A multilayer stent configured for implantation in a body lumen, including a tubular outer layer comprising a first plurality of struts defining an outer layer mesh pattern extending between first and second ends of the outer layer, and a tubular inner layer comprising a second plurality of struts defining an inner layer mesh pattern extending between first and second ends of the inner layer. The inner-layer is at least partially disposed within the outer layer, wherein at least a portion of the inner layer is attached to, or integrally formed with, at least a portion of the outer layer.

13 Claims, 14 Drawing Sheets

(51) Int. Cl.
*A61F 2/90* (2013.01)
*A61F 2/852* (2013.01)
*A61F 2/915* (2013.01)

(52) U.S. Cl.
CPC ... *A61F 2002/823* (2013.01); *A61F 2240/001* (2013.01)

(56) References Cited

U.S. PATENT DOCUMENTS

| | | | |
|---|---|---|---|
| 5,378,237 | A | 1/1995 | Boussignac et al. |
| 5,487,739 | A | 1/1996 | Aebischer et al. |
| 5,772,669 | A | 6/1998 | Vrba |
| 5,776,097 | A | 7/1998 | Massoud |
| 5,833,650 | A | 11/1998 | Imran |
| 5,967,970 | A | 10/1999 | Cowan et al. |
| 6,007,573 | A | 12/1999 | Wallace et al. |
| 6,013,085 | A | 1/2000 | Howard |
| 6,096,021 | A | 8/2000 | Helm et al. |
| 6,206,868 | B1 | 3/2001 | Parodi |
| 6,306,154 | B1 | 10/2001 | Hudson et al. |
| 6,348,063 | B1 | 2/2002 | Yassour et al. |
| 6,432,128 | B1 | 8/2002 | Wallace et al. |
| 6,450,989 | B2 | 9/2002 | Dubrul et al. |
| 6,517,514 | B1 | 2/2003 | Campbell |
| 6,527,919 | B1 | 3/2003 | Roth |
| 6,558,356 | B2 | 5/2003 | Barbut |
| 6,565,552 | B1 | 5/2003 | Barbut |
| 6,592,616 | B1 | 7/2003 | Stack et al. |
| 6,623,471 | B1 | 9/2003 | Barbut |
| 6,626,886 | B1 | 9/2003 | Barbut |
| 6,641,573 | B1 | 11/2003 | Paradi |
| 6,656,152 | B2 | 12/2003 | Putz |
| 6,702,843 | B1 | 3/2004 | Brown et al. |
| 6,849,085 | B2 | 2/2005 | Marton |
| 6,922,579 | B2 | 7/2005 | Taimisto et al. |
| 6,989,024 | B2 | 1/2006 | Hebert et al. |
| 7,137,993 | B2 | 11/2006 | Acosta et al. |
| 7,192,440 | B2 | 3/2007 | Andreas |
| 7,335,227 | B2 | 2/2008 | Jalisi |
| 7,335,426 | B2 | 2/2008 | Martin et al. |
| 7,491,226 | B2 | 2/2009 | Palmaz et al. |
| 7,641,680 | B2 | 1/2010 | Palmaz et al. |
| 7,736,687 | B2 | 6/2010 | Sims et al. |
| 2002/0013616 | A1 | 1/2002 | Carter et al. |
| 2003/0168068 | A1 | 9/2003 | Poole et al. |
| 2004/0260380 | A1 | 12/2004 | Marco et al. |
| 2005/0059957 | A1 | 3/2005 | Campbell et al. |
| 2005/0182436 | A1 | 8/2005 | Chopra |
| 2005/0192662 | A1* | 9/2005 | Ward ............... A61F 2/91 623/1.16 |
| 2006/0025845 | A1 | 2/2006 | Escamilla et al. |
| 2006/0142851 | A1* | 6/2006 | Molaei ............... A61F 2/07 623/1.44 |
| 2007/0027521 | A1 | 2/2007 | Andreas et al. |
| 2007/0088368 | A1 | 4/2007 | Acosta et al. |
| 2007/0118202 | A1 | 5/2007 | Chermoni |
| 2007/0156223 | A1 | 7/2007 | Vaughan |
| 2007/0178221 | A1 | 8/2007 | Sims et al. |
| 2007/0276470 | A1* | 11/2007 | Tenne ............... A61B 17/12022 623/1.38 |
| 2008/0039785 | A1 | 2/2008 | Chopra |
| 2008/0071346 | A1 | 3/2008 | Brown |
| 2008/0077229 | A1 | 3/2008 | Andreas et al. |
| 2008/0097574 | A1 | 4/2008 | Andreas et al. |
| 2008/0208311 | A1 | 8/2008 | Kao et al. |
| 2008/0234798 | A1 | 9/2008 | Chew et al. |
| 2008/0255653 | A1 | 10/2008 | Schkolnik |
| 2010/0137966 | A1 | 6/2010 | Magnuson |
| 2010/0318171 | A1 | 12/2010 | Porter et al. |
| 2010/0318180 | A1* | 12/2010 | Porter ............... A61F 2/91 623/1.16 |
| 2012/0259404 | A1* | 10/2012 | Tieu ............... A61F 2/852 623/1.15 |

FOREIGN PATENT DOCUMENTS

| | | |
|---|---|---|
| WO | 96/38109 | 12/1996 |
| WO | 2004012785 | 2/2004 |
| WO | 2004110521 | 12/2004 |
| WO | 2005/042057 | 5/2005 |
| WO | 2005122960 | 12/2005 |
| WO | 2007005799 | 1/2007 |
| WO | 2007117645 | 10/2007 |
| WO | 2008033177 | 3/2008 |

OTHER PUBLICATIONS

Non final Office Action dated Jun. 15, 2007, for related U.S. Appl. No. 10/782,359, filed Feb. 18, 2004, Inventor Gopal K. Chopra (6 pages).

Papers from file history for related application U.S. Appl. No. 11/872,555, filed Oct. 15, 2007, Inventor Gopal Chopra, including (20 pages total): Amendment Response to Non Final Office Action dated Dec. 24, 2009, for U.S. Appl. No. 11/872,555, dated Mar. 19, 2010; Non Final Office Action for U.S. Appl. No. 11/872,555, dated Dec. 24, 2009.

PCT International Search Report and Written Opinion for PCT/US2010/037809, Applicant Boston Scientific Scimed, Inc., Forms PCT/ISA/210, 220, and 237 dated Sep. 15, 2010 (14 pages).

PCT International Search Report and Written Opinion for PCT/US2010/037831, Applicant Boston Scientific Scimed, Inc., Forms PCT/ISA/210, 220, and 237 dated Sep. 15, 2010 (15 pages).

Non Final Office Action dated Feb. 13, 2012 for U.S. Appl. No. 12/796,562, filed Jun. 8, 2010, Inventor Stephen Porter (10 pages).

Non Final Office Action dated Apr. 25, 2012, for U.S. Appl. No. 12/796,108, filed Jun. 8, 2010, Inventor Stephen Porter (7 pages).

Amendment and Response to Office Action dated May 17, 2012, for U.S. Appl. No. 12/796,108, filed Jun. 8, 2010, Inventor Stephen Porter (6 pages).

Final Office Action dated Jun. 15, 2012, for U.S. Appl. No. 12/796,108, filed Jun. 8, 2010, Inventor Stephen Porter (10 pages).

PCT International Search Report and Written Opinion for PCT/US2013/077631, Applicant Stryker Corporation, Forms PCT/ISA/210, 220, and 237, dated Mar. 28, 2014 (12 pages).

\* cited by examiner

MULTILAYER STENT

RELATED APPLICATION DATA

The present application claims the benefit under 35 U.S.C. § 119 to U.S. provisional patent application Ser. Nos. 61/745,913, filed Dec. 26, 2012, and 61/784,798, filed Mar. 14, 2013. The foregoing applications are hereby incorporated by reference into the present application in their entirety.

FIELD OF THE INVENTION

The inventions disclosed herein are in the field of medical endoprostheses or stents, and more particularly pertain to multilayer stents, methods for making such multilayer stents, and apparatus and methods for delivering and implanting such multiplayer stents in a patient's vasculature or other body lumens.

BACKGROUND

Flow diverting stents have been suggested for delivery during neuro-interventional procedures, e.g., to provide a scaffold across wide necked aneurysms. Once introduced within a blood vessel across the neck of an aneurysm, the mesh of the stent may disrupt blood flow into the aneurysm. For example, the mesh may have a porosity intended to disrupt flow into the aneurysm, yet maintain patency of side branches and/or perforating arteries extending from the blood vessel within which the stent is implanted.

Braided stents, in particular, have been suggested for such applications. Such stents may conform well to tortuous anatomy and/or may provide relatively uniform porosity. However, braided stents also tend to foreshorten substantially upon deployment, which may make accurate deployment difficult and/or may make the trackability of long stents problematic. Although the porosity of a braided stent may be controlled by the number of wires used, increasing the number of wires can increase the profile of the stent, which may make delivery more difficult, e.g., due to increased stiffness of the stent and/or a larger catheter being needed to deliver the stent.

It has also been suggested to deliver multiple stents into a vessel across an aneurysm, e.g., such that a desired porosity may be attained based on the overlapping mesh patterns of the stents. However, this requires delivering individual stents in succession, which can extend and/or otherwise complicate the procedure. Therefore, stents for delivery within body lumens, e.g., flow diverting stents for delivery within vessels across aneurysms, would be useful.

SUMMARY

The disclosed inventions are directed to tubular endoprostheses or stents, and more particularly to multilayer stents, methods for making such multilayer stents, and apparatus and methods for delivering and implanting such multilayer stents into a patient's vasculature or other body lumens.

In one embodiment, there is provided a multilayer stent configured for implantation in a body lumen. The multilayer stent includes a tubular outer layer comprising a first plurality of struts defining an outer layer mesh pattern extending between first and second ends of the outer layer, and a tubular inner layer comprising a second plurality of struts defining an inner layer mesh pattern extending between first and second ends of the inner layer. The inner-layer is at least partially disposed within the outer layer, wherein at least a portion of the inner layer is attached to, or integrally formed with, at least a portion of the outer layer. Together, the outer layer mesh pattern and the inner layer mesh pattern define a porosity of the stent.

By way of non-limiting example, the inner layer and outer layer may be formed from a single piece of material. By way of another example, the inner layer and outer layer may be formed from separate pieces of material, and attached to one another at a plurality of fixation points. By way of yet another example, the multilayer stent may be created using a deposition process.

In one embodiment, one of the first plurality of struts and second plurality of struts comprises helical struts extending in a clockwise direction relative to an axis of the stent, and the other of the first plurality of struts and second plurality of struts comprises helical struts extending in a counter-clockwise direction relative to the stent axis, such that struts of the first plurality cross at an angle over struts of the second plurality.

In various embodiments, the outer layer includes a proximal anchoring portion extending proximally from the first end of outer layer, and a distal anchoring portion extending distally from the second end of outer layer, and the inner layer further comprising a proximal anchoring portion extending proximally from the first end of inner layer, and a distal anchoring portion extending distally from the second end of inner layer, wherein the proximal and distal anchoring portions of the inner layer are attached to, or integrally formed with, the respective proximal and distal anchoring portions of the outer layer. By way of non-limiting examples, the respective proximal and distal anchoring portions of the inner and outer layers may all be formed from a single tubular piece of material, or through a deposition process. Alternatively, the inner layer and outer layer may be formed from separate pieces of material, wherein the proximal anchor portion of the inner layer is attached to the proximal anchor portion of the outer layer at a first plurality of fixation points, and the distal anchor portion of the inner layer is attached to the distal anchor portion of the outer layer at a second plurality of fixation points, and wherein the first plurality of struts defining the outer layer mesh pattern are not connected to the second plurality of struts defining the inner layer mesh pattern outside of the respective anchor portions, such that the struts of the respective outer layer and inner layer mesh patterns remain free to move relative to one another. In some embodiments, the respective proximal anchoring portions and distal anchoring portions of the outer layer and inner layer comprise respective struts that overly one another such that struts of the proximal anchoring portion of the outer layer are aligned over respective struts of the proximal anchoring portion of the inner layer, and struts of the distal anchoring portion of the outer layer are aligned over respective struts of the distal anchoring portion of the inner layer.

In one embodiment, the multilayer stent has a delivery configuration sized for introduction into a body lumen, and an expanded configuration for implantation in the body lumen, wherein the stent is biased to the expanded configuration, and wherein the outer layer mesh pattern and inner layer mesh pattern together define a porosity through a sidewall of the stent that includes an open area between about fifty and ninety percent (50-90%) in the expanded configuration.

In some embodiments, the multilayer stent includes a plurality of flexible fixation points coupling struts of the first plurality to adjacent struts of the second plurality at discrete locations.

In some embodiments, the multilayer stent includes one or more features formed on at least one of an outer surface of the inner layer and an inner surface of the outer layer to reduce sliding motion of struts of the first plurality relative to struts of the second plurality.

In accordance with another aspect of the disclosed inventions, various methods for making a multilayer stent are disclosed.

In one embodiment, a method for making a multilayer stent from a tubular body includes: (i) creating a circumferential space within a wall of the tubular body spaced apart from the first and second end regions, thereby creating a central region including an outer layer and an inner layer; and (ii) forming a respective plurality of struts in each of the outer and inner layers to provide a multilayer central portion, including a first plurality of struts defining an outer-layer mesh pattern, and a second plurality of struts defining an inner-layer mesh pattern. This method may further include (iii) forming a further respective plurality of struts in each of the first and second end regions to provide respective anchoring end portions of the stent.

In another embodiment, a method for making a multilayer stent includes: (i) forming a tubular outer member comprising a first plurality of struts defining an outer member mesh pattern extending between first and second ends of the outer member; (ii) forming a tubular inner member comprising a second plurality of struts defining an inner member mesh pattern extending between first and second ends of the inner member; (iii) positioning the inner member so as to be at least partially disposed within the outer member; and (iv) fixing the outer and inner members together at discrete locations. \

Notably, the tubular outer member may further include a proximal anchoring portion extending proximally from the first end of outer member, and a distal anchoring portion extending distally from the second end of outer member, and the tubular inner member further may further include a proximal anchoring portion extending proximally from the first end of inner member, and a distal anchoring portion extending distally from the second end of inner member, wherein fixing the outer and inner members together at discrete locations comprises attaching the proximal and distal anchoring portions of the outer member layer to the respective proximal and distal anchoring portions of the inner member. In such embodiments, the proximal anchor portion of the outer member may be attached to the proximal anchor portion of the inner member at a first plurality of fixation points, and the distal anchor portion of the outer member may be attached to the distal anchor portion of the inner member at a second plurality of fixation points, wherein the first plurality of struts defining the outer member mesh pattern are not connected to the second plurality of struts defining the inner member mesh pattern outside of the respective anchor portions, such that the struts of the respective outer member and inner member mesh patterns remain free to move relative to one another. In one such embodiment, the respective proximal anchoring portions and distal anchoring portions of the outer member and inner member comprise respective struts that overly one another such that struts of the proximal anchoring portion of the outer member are aligned over respective struts of the proximal anchoring portion of the inner member, and struts of the distal anchoring portion of the outer member are aligned over respective struts of the distal anchoring portion of the inner member.

In yet another embodiment, a method for making a multilayer stent includes (i) depositing a first sacrificial layer onto an outer surface of a core to create a pattern of first recesses between regions of the first sacrificial layer corresponding to a desired mesh pattern for a first stent layer; (ii) depositing stent material to substantially fill the first recesses, thereby forming a plurality of first struts within the first recesses; (iii) removing excess stent material from the first struts to define the first stent layer; (iv) depositing a second sacrificial layer over the first sacrificial layer and the first stent layer to create a pattern of second recesses between regions of the second sacrificial layer corresponding to a desired mesh pattern for a second stent layer; (v) depositing stent material to substantially fill the second recesses, thereby forming a plurality of second struts within the second recesses; (vi) removing excess stent material from the second struts to define the second stent layer; and (vii) removing the first and second sacrificial layers. This method may further include (viii) depositing a sacrificial separation layer over at least a portion of the first sacrificial layer and the first stent layer before depositing the second sacrificial layer; and (ix) removing the sacrificial separation layer, such that at least some of the first and second struts of the first and second stent layers are independently movable relative to one another.

These and other aspects of the disclosed inventions will be apparent from the following detailed description, and the appended claims, particularly when considered in conjunction with the accompanying drawings in which like parts bear like reference numerals.

BRIEF DESCRIPTION OF THE DRAWINGS

The drawings illustrate exemplary embodiments, in which.

DETAILED DESCRIPTION

Figure 1:
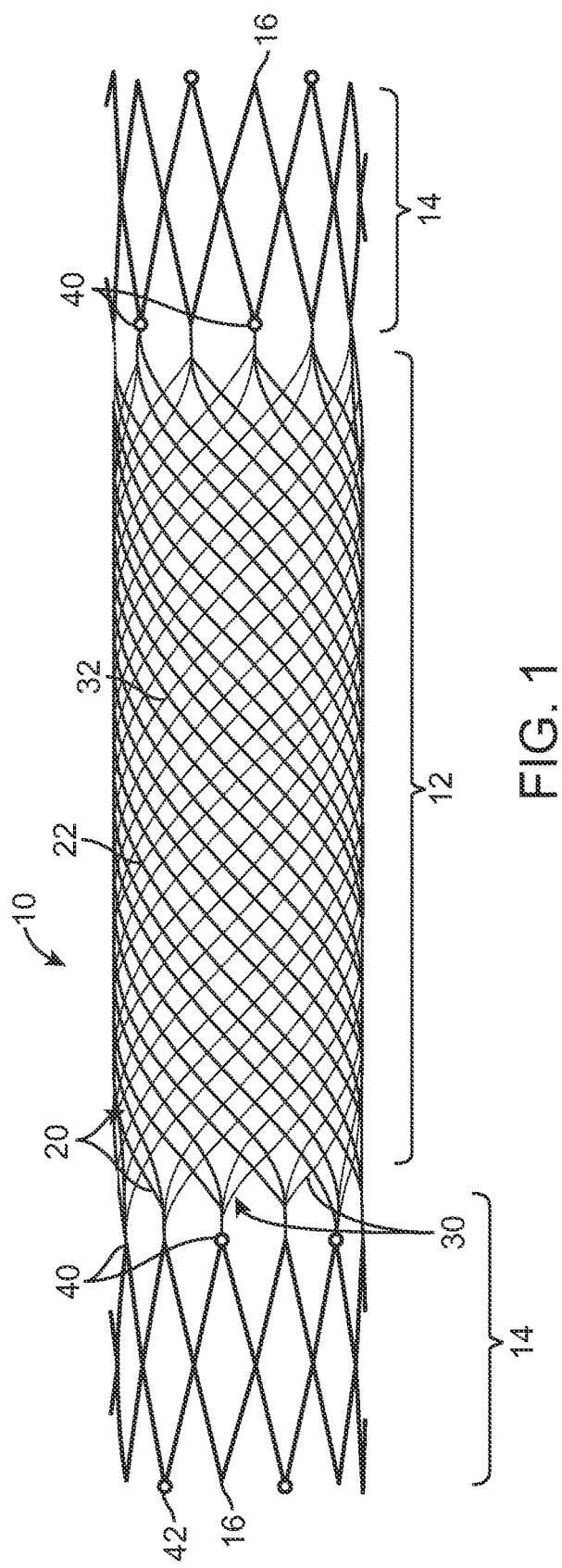
FIG. 1 is a side view of an exemplary embodiment of a multilayer stent.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of, or as a limitation on the scope of, the disclosed inventions, which are defined only by the appended claims and their equivalents. In addition, an illustrated embodiment of the disclosed inventions needs not have all the aspects or advantages shown, and an aspect or an advantage described in conjunction with a particular embodiment of the disclosed inventions is not necessarily limited to that embodiment and can be practiced in any other embodiments even if not so illustrated.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. All numeric values are herein assumed to be modified by the term "about," whether or not explicitly indicated. The terms "about" and "approximately" generally refer to a range of numbers that one of skill in the art would consider equivalent to the recited value (i.e., having the same function or result). In many instances, the terms "about" and "approximately" may include numbers that are rounded to the nearest significant figure. As used in this specification and the appended claims, numerical ranges include both endpoints and all numbers included within the range. For example, a range of 1 to 5 inches includes, without limitation, 1, 1.5, 2, 2.75, 3, 3.80, 4 and 5 inches.

Figure 2A:
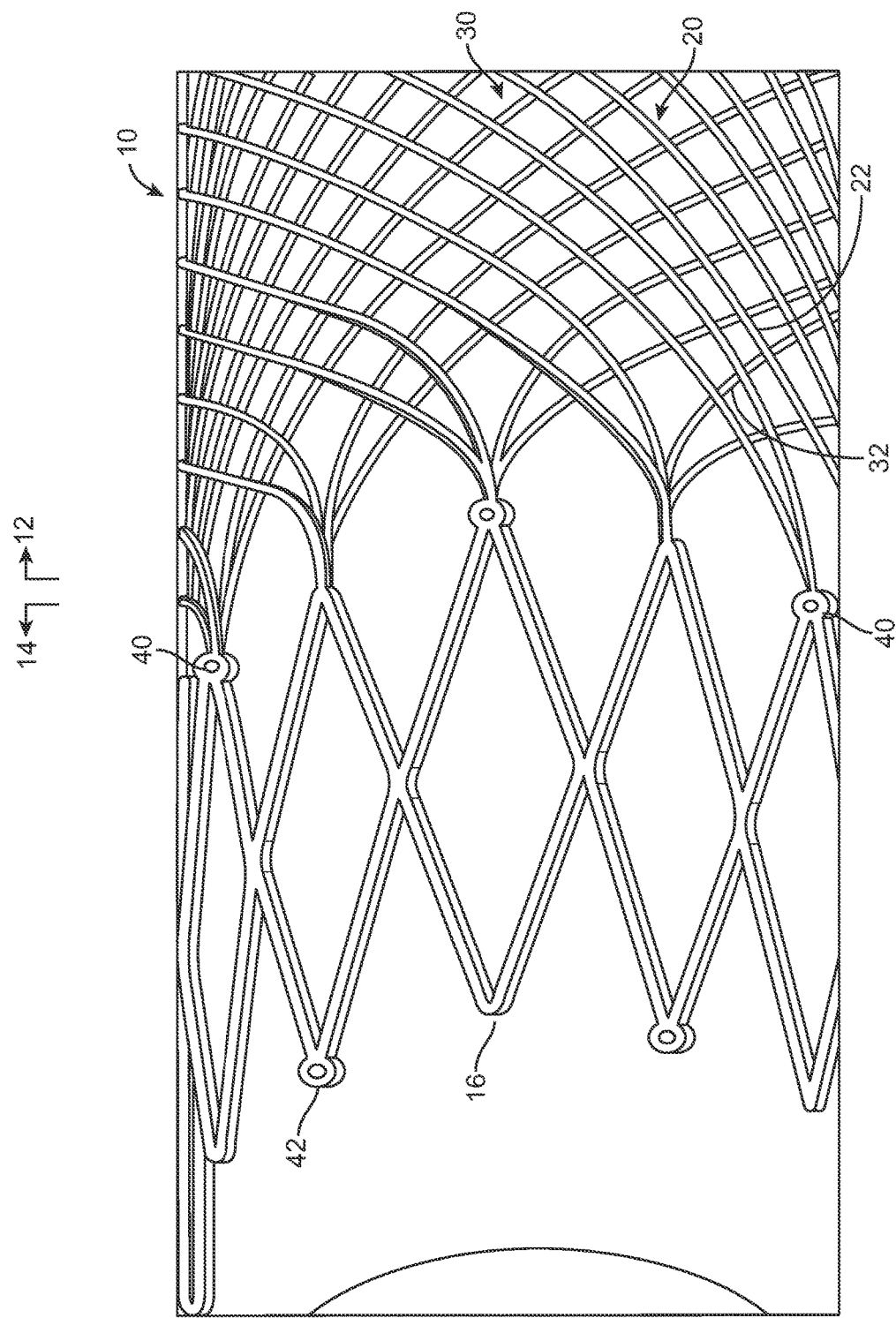
FIG. 2A is a perspective detail of one end of the stent of FIG. 1.
Figure 2B:
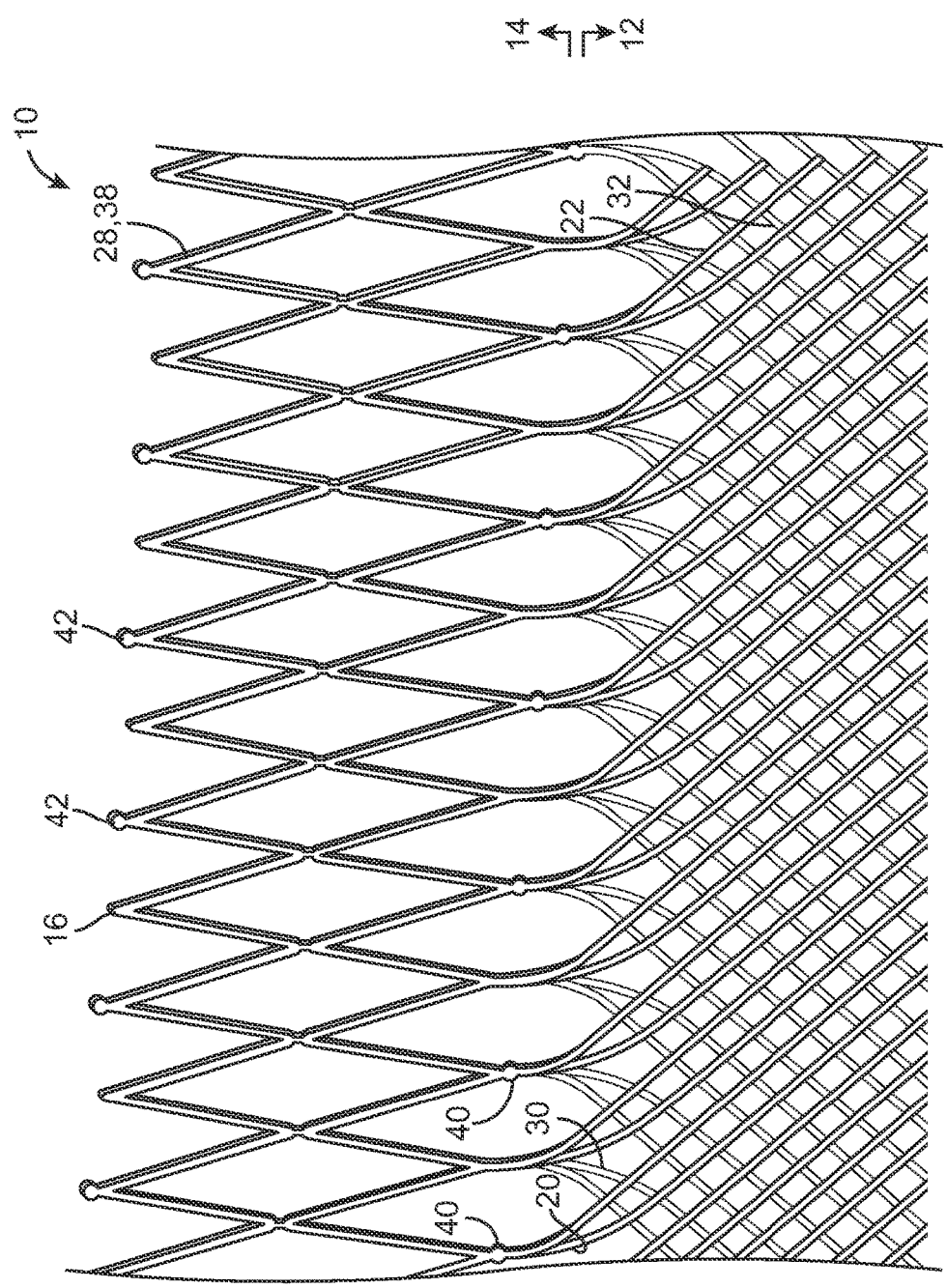
FIG. 2B is a flat pattern detail of the end of the stent of FIGS. 1 and 2A.

Turning to the drawings, FIGS. 1, 2A and 2B illustrate an exemplary embodiment of a multi-layer stent or tubular prosthesis 10 that includes an outer tubular member or layer 20, an inner tubular member or layer 30 disposed within and adjacent the outer member 20, and a plurality of fixation points 40 fixing or attaching together the outer and inner members 20, 30 at discrete locations, as further described herein. It will be appreciated that alternate embodiments of the multi-layer stent 10 may include more than two layers, if desired, e.g., three, four, or more layers (not shown), instead of only the outer and inner layers, 20 and 30. The multiple layers are preferably disposed concentrically, i.e., such that the layers are disposed within one another, rather than in a braided or other arrangement, in which elements of one layer are interwoven with elements of another. The resulting configuration of concentric layers may provide an effective porosity for the resulting multi-layer stent, i.e., a percentage of open area of the sidewall of the stent, which is less than the open area of each individual layer, as described further below.

The two layer stent 10 generally includes a central portion 12 and respective anchoring portions 14 located on either side of the central portion 12. Optionally, the anchoring portions 14 may be omitted, and the entire stent 10 may be formed from the central portion 12, e.g., as described elsewhere herein. As shown, the outer and inner members 20, 30 each extends over the entire length of the stent 10, e.g., from the tips 16 of one anchoring portion 14 through the central portion 12 to the tips 16 of the other anchoring portion 14. Thus, each of the outer and inner members 20, 30 includes struts or other elements at least partially defining the respective central and anchoring portions 12, 14 of the stent 10.

The outer and inner members 20, 30 may include different struts arrangements within the central and anchoring portions 12, 14, e.g., such that the central portion 12 has different properties than the anchoring portions 14. For example, the central portion 12 may have greater flexibility than the anchoring portions 14 and/or may have different radial strengths or biases, as described further elsewhere herein.

The outer and inner members 20, 30 are attached together at discrete locations on the central and/or anchoring portions 12, 14. As best seen in FIGS. 2A and 2B, the outer and inner members 20, 30 are connected to each other at discrete fixation points (e.g., at every other strut connection) 40 near the transition between the central and anchoring portions 12, 14 of the stent 10. This intermittent arrangement may substantially maintain desired alignment of the outer and inner members 20, 30, while enhancing overall flexibility of the stent 10. For example, within the central portion 12, the outer and inner members 20, 30 are free to move relative to one another, e.g., circumferentially and/or axially, which enhances flexibility of the central portion 122.

In the illustrated embodiment, the outer and inner members 20, 30 are also connected at additional fixation points 42 within the anchoring portions 14, e.g., at the tips 16. As best seen in FIGS. 2A and 2B, the fixation points 42 are located at every other tip 16, although a different arrangement of fixation points may be used, if desired. For example, the outer and inner members 20, 30 may be connected intermittently or substantially continuously along the struts of the anchoring portions 14. Alternatively, if the multiple layers are provided only in the central portion 12 (not shown), the multiple layers may be independent and free to move relative to one another completely within the central portion 12, and fixed together only at the respective ends of the middle portion 12. Further alternatively, separate single-layer anchoring portions may be attached or otherwise coupled to the multiple layer central portion, e.g., having a thickness similar to the effective thickness of the layers of the central portion, or may be integrally formed with the layers of the central portion, as described elsewhere herein.

Figure 3A:
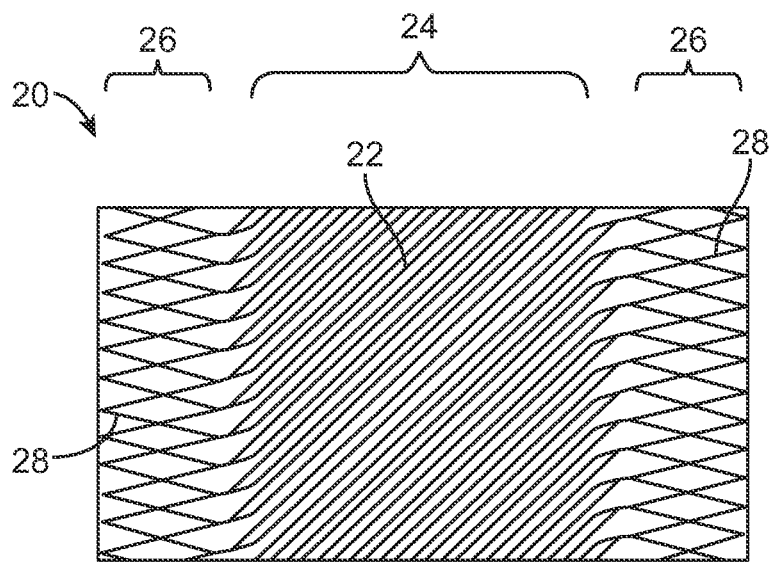
FIGS. 3A and 3B are top views of flat patterns for layers that may be connected together to provide the stent of FIG. 1
Figure 3B:
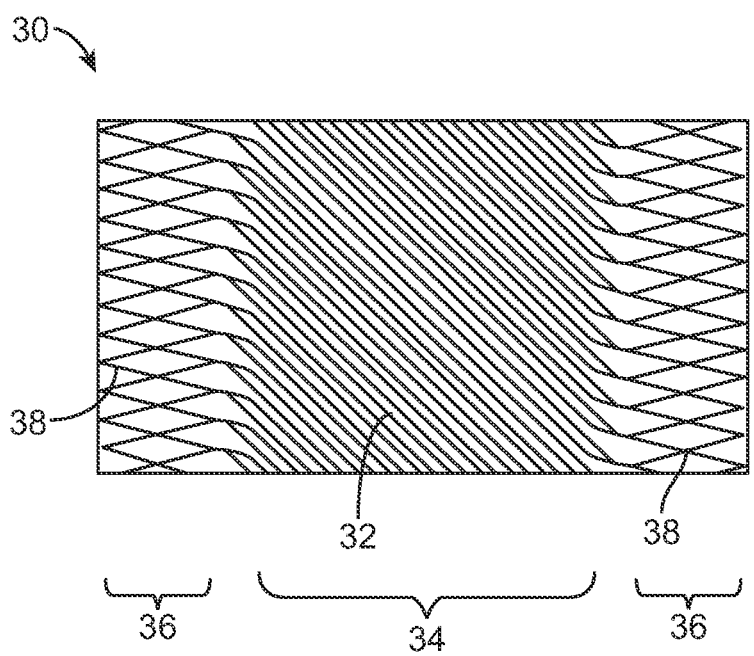
Figure 4:
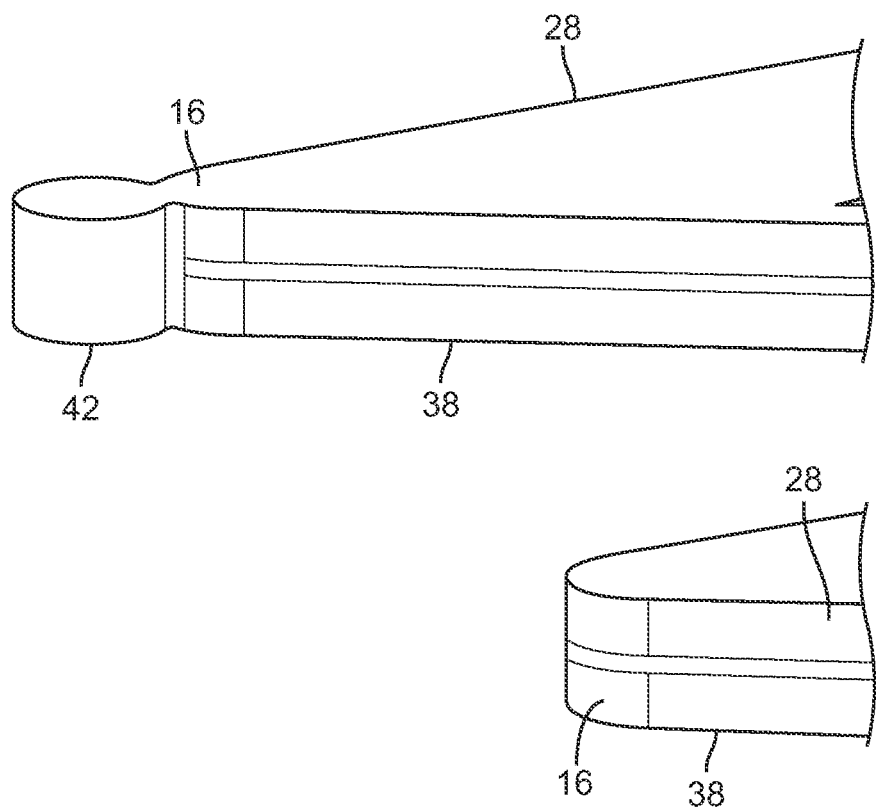
FIG. 4 is a detail of the stent of FIG. 1, showing an exemplary fixation point for connecting layers of the stent together.

Turning to FIG. 3A, the outer member 20 generally includes a plurality of outer struts 22 defining a mesh pattern within the central portion 24 extending between the anchoring portions 26 of the outer member 20. In the exemplary embodiment shown, the outer struts 22 extend diagonally or helically around the circumference of the stent 10, as best seen in FIGS. 1 and 2A. Similarly, as shown in FIG. 3B, the inner member 30 also includes a plurality of inner struts 32 defining a mesh pattern within its central portion 34 extending between the anchoring portions 36 of the inner member 30. In the exemplary embodiment shown, the inner struts 32 also extend diagonally or helically around the circumference of the stent 10; however, the inner struts 32 extend in a different, e.g., opposite, direction to the outer struts 22. Thus, the outer struts 22 may overlap and intersect the inner struts 32 such that the outer and inner mesh patterns together define pores or enclosed openings defining a desired porosity for the sidewall of the central portion 12 of the stent 10. For example, in the embodiment shown in FIG. 1, the outer struts 22 may extend helically in a counterclockwise direction around a central axis extending from the left anchoring portion 14 to the right anchoring portion 14, while the inner struts 22 may extend helically in a clockwise direction, thereby defining diamond shaped pores through the sidewall of the stent 10.

Also as shown in FIG. 3A, the anchoring portions 26 of the outer member 20 may include a plurality of struts 28 defining a zigzag pattern across the width (corresponding to the circumference) of the outer member 20. For example, each anchoring portion 26 may include a plurality of bands of zigzag struts 28 attached together to define a length for the anchoring portion 26. As shown, adjacent bands of zigzag struts 28 may be out of phase with one another such that the anchoring portion 26 defines a generally diamond-shaped mesh pattern. Similarly, the anchoring portions 36 of the inner member 20 may include a plurality of struts 38 defining a zigzag pattern across the width (corresponding to the circumference) of the inner member 30. Alternatively, if desired, other configurations of struts and mesh patterns (not shown) may be provided in the anchoring portions 14, e.g., to provide desired properties, such as flexibility, radial strength, and the like.

Unlike the central portion 12, the struts 28, 38 of the outer and inner members 20, 30 are in phase one another, e.g., defining substantially identical zigzag patterns such that the struts 28 of the outer member 20 are aligned with and overlying respective struts 38 of the inner member 30. Because of the discrete fixation points 40, 42, the struts 28, 38 may have some independent movement relative to one another, which may enhance flexibility of the anchoring portions 14, while generally supporting one another radially to provide greater radial strength, e.g., compared to the central portion 12. Alternatively, if desired, one or more of the outer struts 28 may be attached to respective underlying inner struts 38, e.g., intermittently or substantially continuously along the lengths of the struts 28, 38, which may enhance radial strength and/or rigidity of the anchoring portions 14.

Figure 5:
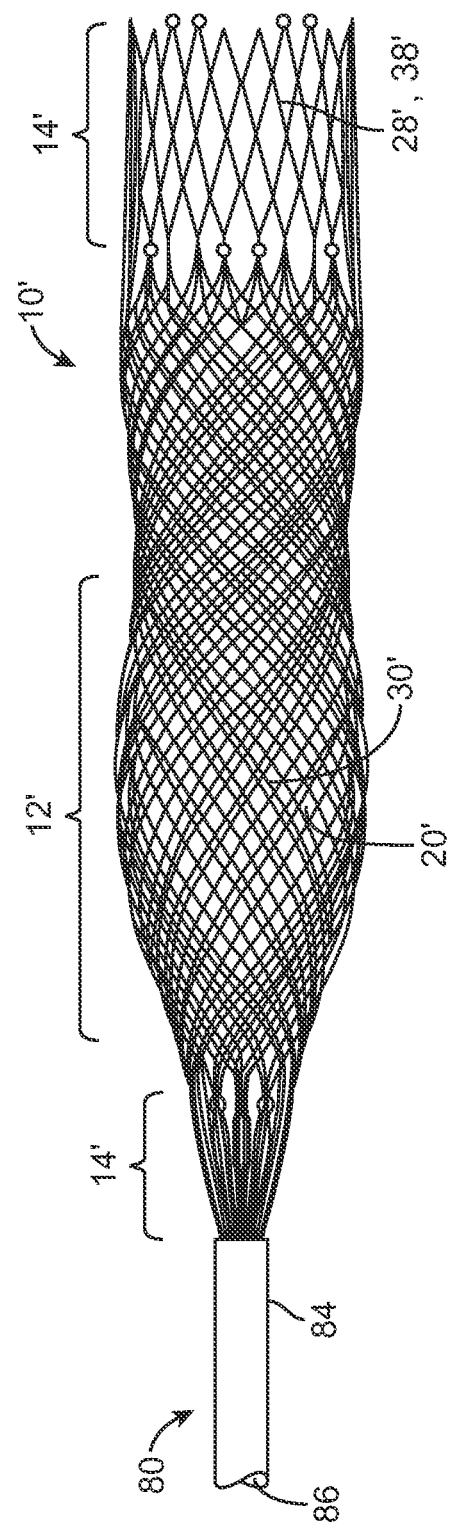
FIG. 5 is a side view of another exemplary embodiment of a multilayer stent being deployed from a delivery catheter.
Figure 7:
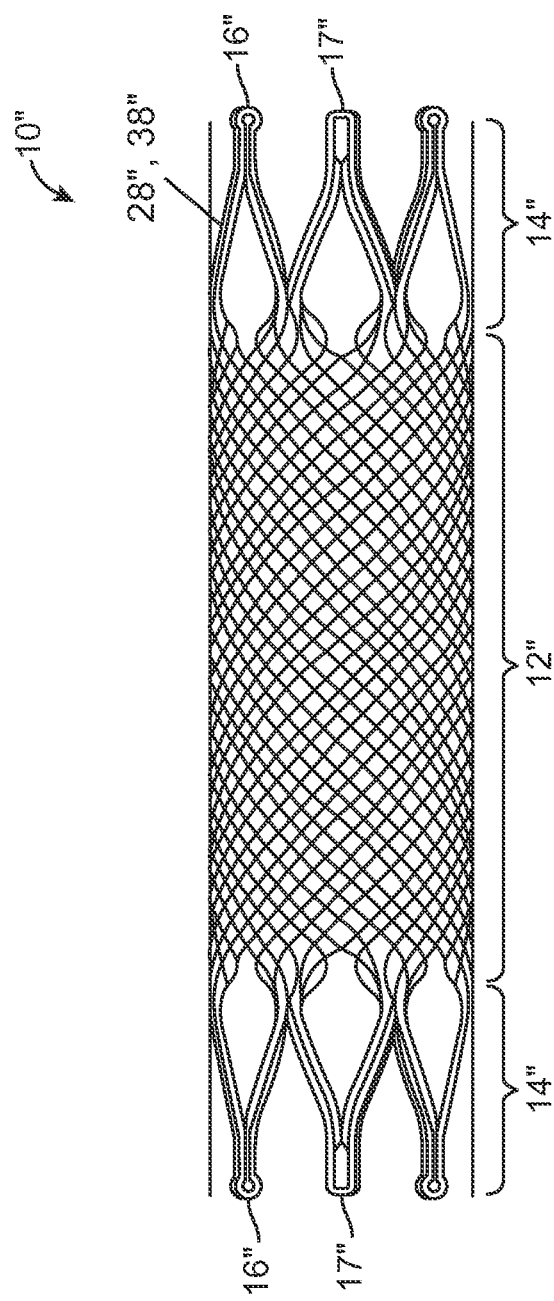
FIG. 7 is a side view of yet another exemplary embodiment of a multilayer stent.

In the embodiment shown in FIGS. 1-2B, each anchoring portion 14 includes two bands of zigzag struts 28, 38 along the length of the anchoring portion 14 and with respective adjacent outer and inner struts 28, 38 aligned and disposed concentrically. Alternatively, it will be appreciated that more or fewer bands may be provided. For example, FIG. 5 shows a stent 10' including four bands of zigzag struts 28,' 38' in each of the anchoring portions 14,' while FIG. 7 shows a stent 10" including only a single band of zigzag struts 28," 38" in each of the anchoring portions 14."

Also as best seen in FIGS. 2A and 2B, each strut connection at the anchoring portions 14 may be coupled to one or more of the struts 22, 32 of the central portion 12. For example, each connection of the outer struts 28 of the anchoring portion 14 may be coupled to two outer struts 22 of the central portion 12, and, similarly, each connection of the inner struts 38 of the anchoring portion 14 may be coupled to two inner struts 32 of the central portion 12. Alternatively, if a different density of struts 22, 32 is desired in the central portion 12, the number of struts 22, 32 coupled to each strut connection 40 of the anchoring portion 14 may be varied, e.g., such that there is one-to-one, three-to-one, or other ratio of struts 22, 32 in the central portion 12 extending from the strut connections.

Returning to FIGS. 3A and 3B, the outer and inner members 20, 30 may be formed from flat sheets, e.g., by etching, laser cutting, machining, or otherwise removing material from a flat sheet to provide the struts 22, 32 and mesh patterns. The resulting flat mesh patterns may be rolled and adjacent edges may be attached, e.g., by one or more of welding, fusing, bonding with adhesive, and the like, to define respective tubular members. Alternatively, the outer and inner members 20, 30 may be formed from tubular bodies, e.g., extruded, machined, drawn, or otherwise formed tubes, from which material is removed to provide the struts 22, 32 and mesh patterns e.g., by etching, laser cutting, machining, or otherwise removing material from the tube wall.

In another alternative, the outer and inner members 20, 30 may be formed by vapor deposition or other deposition methods, e.g., to create the struts 22, 32 and mesh patterns onto separate flat bases (not shown), e.g., to provide flat mesh patterns, or on separate cylindrical mandrels or other forms (also not shown), e.g., to form the outer and inner members 20, 30 as tubular bodies. This alternative may facilitate creating relatively thin-walls, i.e., radial thicknesses for the outer and inner members 20, 30. Exemplary apparatus and methods for making deposited stents are described further elsewhere herein.

Once formed (as rolled and attached flat sheets or as tubular bodies), the outer and inner members 20, 30 may be processed, e.g., to provide desired properties and/or finishes for the final stent 10. For example, the outer and inner members 20, 30 may be heat treated, e.g., such that they and the final stent 10 are biased to a first diameter or configuration and may be resiliently directed to another diameter or configuration. For example, the stent 10 may be biased to an expanded or relaxed configuration, yet may be resiliently compressed to a contracted or delivery configuration, e.g., for introduction into a patient's body, as described further elsewhere herein.

In an exemplary embodiment, the outer and inner members 20, 30 may be formed from Nitinol or other superelastic material that may be constrained in the delivery configuration and may be biased to return elastically towards the relaxed configuration upon deployment. Alternatively, the outer and inner members 20, 30 may be formed from other materials, e.g., stainless steel, Elgiloy, or other metals, plastic materials, composite materials, and the like.

In exemplary embodiments, the stent 10 may have an expanded or relaxed diameter between about 1.5 and six millimeters (1.5-6.0 mm), and may be compressible to a contracted or delivery configuration between about 0.4 to 1.5 millimeters (0.4-1.5 mm). In addition, each of the outer and inner members 20, 30 may have a substantially uniform radial thicknesses, e.g., between about 0.01 and 0.07 millimeter (0.01-0.07 mm).

In an alternative embodiment, the stent 10 may be heat treated to provide different properties between the central portion 12 and the anchoring portions 14. For example, the outer and inner members 20, 30 may be heat treated such that the central portion 12 is biased to a first diameter, e.g., corresponding to a body lumen within which the stent 10 may be deployed, while the anchoring portions 14 may be biased to a second diameter larger than the first diameter, e.g., such that the anchoring portions 14 may apply an outward force against the wall of a body lumen, as described further elsewhere herein.

In addition, the outer and inner members 20, 30 may be electropolished or otherwise treated, e.g., to remove sharp edges along the struts, connections, and/or fixation points, as desired. Optionally, one or more surface of the outer and/or inner members 20, 30 may be coated with one or more desired materials, also as described elsewhere herein.

Such processing may be completed before or after the outer and inner members 20, are attached together. For example, the outer and inner members 20, 30 may be attached together, e.g., by welding, fusing, bonding with adhesive, and/or riveting at the fixation points 40, 42, and then the assembled stent 10 may be heat treated and/or otherwise processed. In another embodiment, fixation points 40, 42 may be created by laminating or depositing additional material at the desired locations for the fixation points 40, 42. For example, a relatively compliant material, e.g., parylene or other polymer, may be applied to the locations for the fixation points 40, 42, which may fix the outer and inner members 20, 30 from substantial translation relative to one another, but allow rotation of struts adjacent the fixation points 40, 42.

Optionally, flexible fixation points may be provided at one or more locations along the central portion 12 of the stent 10 (not shown). In yet another embodiment, the outer and inner members 20, 30 may be attached together using one or more filaments, e.g., sutures, wires, and the like (not shown), which may be used to attach adjacent struts of the outer and inner members 20, 30 at discrete locations, e.g., within the central portion 12 and/or the anchoring portions 14. Alternatively, such filament(s) may be woven between the outer and inner members 20, 30, e.g., around the circumference of the stent 10 at the respective junctions between the central portion 12 and the anchoring portions 14 or elsewhere in the stent 10, e.g., to provide fixed or flexible fixation points. The ends of the filament(s) may be secured by one or more of knotting, bonding with adhesive, fusing, and the like.

Figure 6:
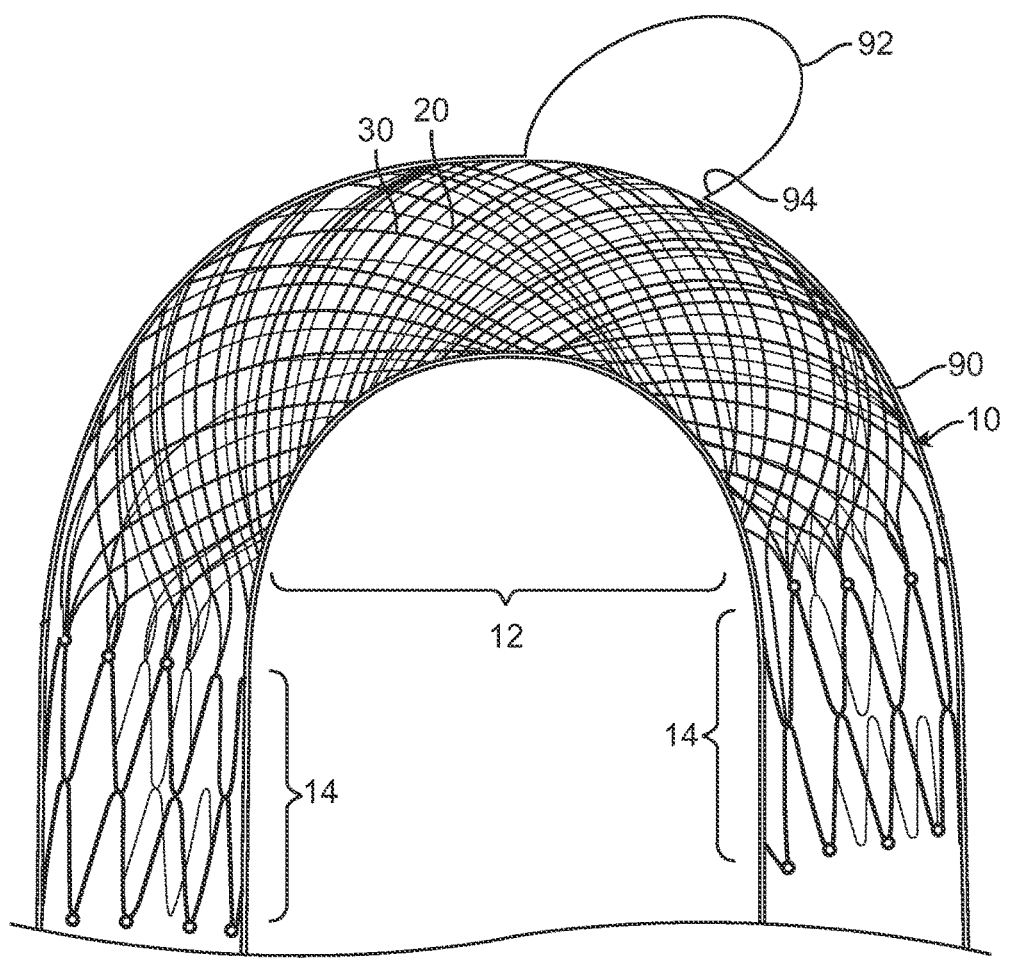
FIG. 6 is a cross-sectional view of a body lumen within a patient's body showing the stent of FIG. 1 delivered within the body lumen.

Such flexible fixation points may enhance maintaining substantially uniform porosity along the central portion 12, e.g., if the stent 10 is bent, for example, as shown in FIG. 6. Such flexible fixation points may pin the coupled struts from substantial translation axially or circumferentially (which may otherwise increase or decrease the local porosity if the struts slide relative to one another) yet allow the coupled struts to rotate and maintain flexibility of the stent 10.

Alternatively, the outer and inner members 20, 30 may be processed separately, e.g., if desired to provide different properties between the layers, and then attached together, e.g., using the methods just described. If processed separately, the inner member 30 may be provided with a diameter slightly smaller than the outer member 20 during heat treatment, e.g., such that the inner member 30 may be introduced into the outer member 20 while maintaining substantially sliding contact between the adjacent surfaces. In this embodiment, no radial forces are applied between the outer and inner members 20, 30.

Alternatively, the outer and inner members 20, 30 may be heat treated or otherwise biased to other diameters, e.g., if desired to impose radial forces between the outer and inner members 20, 30. For example, if the inner member 30 is heat treated to a diameter equal or greater than the outer member 20, and then compressed and inserted into the outer member 20, the outer member 20 may constrain the inner member 30, e.g., to prevent gaps between the layers and/or to increase friction between the outer and inner members 20, 30.

Optionally, other features may be provided on the stent 10, if desired. For example, one or more radiopaque or other markers (not shown) may be attached, applied, or otherwise incorporated into the stent 10 at desired locations, e.g., at the tips 16, or at the junctions between the central and anchoring portions 12, 14. In the exemplary stent 10" shown in FIG. 7, markers 17" are provided in the tips 16." For example, loops may be provided on the tips 16," which may be filled with radiopaque material to enhance identification of the tips 16" using fluoroscopy or other external imaging. In addition or alternatively, radiopaque coatings may be applied to the material of the outer and/or inner members 20, 30, and/or the material itself may be radiopaque.

In addition or alternatively, if desired, one or more features (not shown) may be provided on the contact surfaces of the outer and inner members 20, 30. For example, a plurality of spaced-apart protrusions (not shown) may be provided on the outer surface of the inner member 30 and/or on the inner surface of the outer member 20 that may increase friction and/or other contact between the outer and inner members 20, 30. Such features may minimize sliding motion, yet allow the contact points to rotate or otherwise move, as needed, to accommodate introduction and/or deployment. In an exemplary embodiment, such protrusions may be formed by depositing additional material at discrete locations on the desired surfaces, e.g., similar to or different than the base material of the outer and inner members 20, 30. Such protrusions may be deposited after forming the outer and inner members 20, 30, e.g., after being formed from a flat sheet or tube, or during formation of the outer and inner members 20, 30, e.g., during a deposition process, as described further elsewhere herein. The material for the protrusions may be similar to the base material of the outer and inner members 20, 30 or different, e.g., having different frictional or other mechanical properties, if desired.

Once the outer and inner members 20, 30 are formed, attached together, and/or processed, the final stent 10 (or any of the other embodiments herein) may then be stored and/or otherwise prepared for eventual implantation within a patient's body. The resulting stent 10 may be particularly useful for implantation within a patient's neurovasculature, e.g., within a blood vessel adjacent to an aneurysm, as shown in FIG. 6. Alternatively, the resulting stent structure may be used for other deployable and/or recoverable devices. For example, the multilayer stent structure could be incorporated into a clot removal apparatus (not shown), in which the multiple layers may sheer clot and/or pinch or otherwise engage clot received within the interior of the stent structure, e.g., to allow the clot to be removed from a vessel or other body lumen (also not shown).

For example, in an exemplary embodiment, a delivery catheter, such as micro-catheter 80 shown in FIG. 5, may be used for introducing a stent, such as stent 10' into a patient's vasculature. Generally, the catheter 80 includes a proximal end (not shown), a distal end 84 sized for introduction into a patient's body, e.g., into the neurovasculature, and a lumen 86 extending therebetween. In exemplary embodiments, the catheter 80 may have an outer diameter between about 0.5 and two millimeters (0.5-2.0 mm), and/or a length between about one hundred ten and one hundred eighty centimeters (110-180 cm).

In an exemplary procedure, the catheter 80 may be employed in an "empty catheter" technique, in which the distal end 84 (without a stent within the lumen 86) of the catheter 80 is introduced into a patient's vasculature from a peripheral entry site (not shown) and advanced into a target vessel, such as the vessel 90 shown in FIG. 6. Because the catheter 80 is not carrying a stent, the distal end 84 may be more easily tracked to the target vessel, e.g., through tortuous anatomy. The catheter 80 may be introduced over a previously placed guidewire and/or through a guide catheter (not shown), if desired, using conventional methods.

Once the distal end 84 is positioned within the vessel 90, e.g., beyond the aneurysm 92, the stent 10 (or any of the embodiments herein) may be loaded into the proximal end of the catheter 80, e.g., from an introducer sheath (not shown), which may constrain the stent 10 in a contracted or delivery condition no larger than the lumen 86 of the catheter 80. A pusher member (not shown) may be used to advance the stent 10 through the lumen 86 until the stent 10 is positioned within the vessel 90, e.g., such that the central portion 12 extends across a neck 94 of the aneurysm 92. The central portion 12 may be substantially longer than the width of the neck 94, e.g., between about 0.5 and five millimeters (0.5-5.0 mm), e.g., to ensure that the anchoring portions 14 are disposed away from the neck 94.

Optionally, positioning the stent 10 may be monitored using fluoroscopy or other external imaging, e.g., to identify the location of the tips 16 and/or junctions between the central and anchoring portions 12, 14 of the stent 10. Once the stent 10 is positioned at a desired location, the distal end 84 of the catheter 80 may be retracted, with the pusher member preventing the stent 10 from migration, thereby deploying the stent 10 from the distal end 84. As the stent 10 is exposed within the vessel 90, the stent 10 may resiliently expand outwardly, e.g., similar to the stent 10' shown in FIG. 5, against the wall of the vessel 90. Once fully deployed, the anchoring portions 14 may engage the wall of the vessel 90 with the central portion 12 extending completely across the neck 94 of the aneurysm 92, as shown in FIG. 6. The catheter 80 and pusher member may then be removed from the patient's body.

In an alternative procedure, the stent 10 may be loaded into the distal end 84 of the catheter 80, e.g., during manufacturing or immediately before implantation, and introduced into the patient's body together. In this alternative, a pusher member (not shown) may be provided within the catheter 80 to facilitate deployment of the stent 10 once positioned at the desired location, as described above.

Once deployed within the vessel 90, the porosity of the central portion 12 may disrupt flow of blood or fluid into the aneurysm 92. However, the porosity may also accommodate continued blood flow through side branches, perforating arteries, and the like (not shown) within the vessel 90, which may also be covered by the central portion 12. In exemplary embodiments, the porosity of the central portion 12 with the stent 10 in its deployed configuration within a vessel 90 may result in an open area (porosity) through the sidewall between about fifty and ninety percent (50-90%), such that the coverage area of the struts is between about ten and fifty percent (10-50%).

The central portion 12 may be sized to apply minimal or no radial forces against the contacted wall of the vessel 90. Alternatively, the central portion 12 may have sufficient radial strength and/or outward bias to engage the wall of the vessel 90 and/or to prevent recoil or collapse of the vessel 90. Even though the struts 28, 38 of the anchoring portions 14 have substantially greater open area than the central portion 12, the configuration of the struts 28, 38, e.g., concentric support of the outer and inner struts 28, 38 and/or the diamond mesh or other mesh configuration, may enhance radial support. Thus, although the anchoring portions 14 may have less scaffolding density than the central portion 12, the anchoring portions 14 may provide sufficient forces and/or engagement against the wall of the vessel 90 to secure the stent 10 within the vessel 90.

The central portion 12 of the stent may not apply substantial radial forces outwardly against the vessel wall. In contrast, the anchoring portions 14 may apply sufficient radial force to engage the wall of the vessel 90 and prevent migration of the stent 10. Optionally, if desired, a secondary balloon catheter or other expandable device (not shown) may be introduced into the deployed stent 10 and expanded, e.g., to further dilate the anchoring portions 14 of the stent 10 and/or surrounding anatomy.

The helical configuration of struts 22, 32 within the central portion 12 of the stent 10, as shown in FIGS. 1-3B, may provide additional advantages for the stent 10. For example, the overlapping helical configuration may minimize foreshortening of the stent 10 as it expands from its delivery to deployed diameter. In addition, the opposing directions of the helical struts 22, 32 may balance any rotational bias that may otherwise be created within the stent 10, e.g., if the stent 10 is advanced through tortuous anatomy that requires application of torsional forces during advancement. The opposing directions may bias the stent 10 to return towards a substantially neutral torsional state, minimizing twisting or other deformation upon deployment.

The helical configuration or other closed cell strut configurations may also facilitate recapture of the stent 10, e.g., if it is subsequently desirable to remove the stent from the vessel 90. The helical outer struts 22 may provide a substantially smooth outer surface, which may reduce the risk of a recapture catheter or other device (not shown) being introduced and advanced over the stent 10 from catching on the struts 22. Alternatively, if desired, the inner member 30 may include an open cell or other strut configuration (not shown) since the struts 22 of the outer member 30 may still provide a substantially smooth outer surface.

Further, the discrete fixation points may accommodate some relative movement between the outer and inner members 20, 30, e.g., which may increase flexibility during delivery and/or deployment. If the stent 10 includes additional flexible fixation points deposited or otherwise applied along the central portion 12 (not shown), the deposited materials may accommodate rotation to maintain the flexibility and/or bending of the stent 10 without created substantially different local porosity, e.g., between the inside and outside of a bend.

Figure 8:
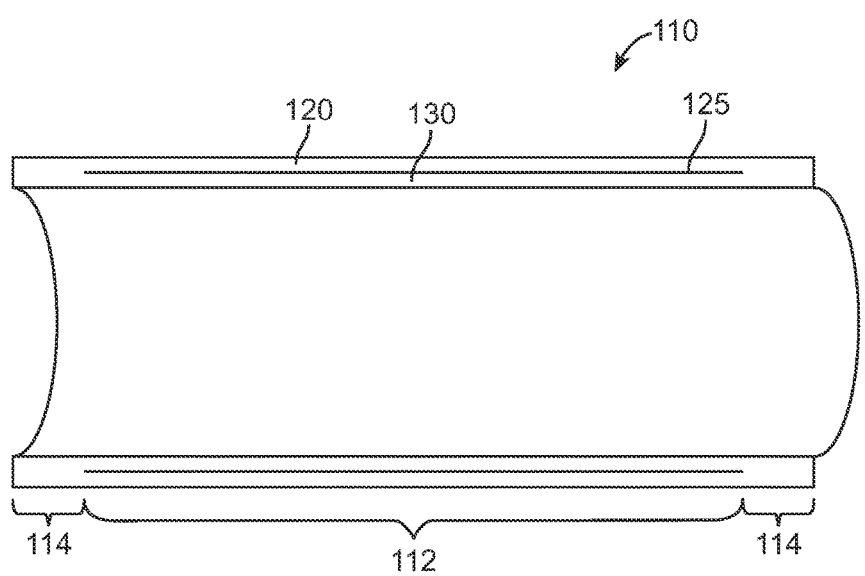
FIG. 8 is a cross-sectional side view of a multiple-layered tubular body that may be used to form a multilayer stent.

Turning to FIG. 8, a multiple layer tubular body 110 is shown, which may be formed into a multi-layer stent, such as any of those described elsewhere herein. Generally, the tubular body 110 may be formed from a single length of tubing, e.g., a section of hypotube having a length corresponding to the overall length of the final stent. As shown, the tubular body 110 includes a hollow-walled section, i.e., a central region 112 including outer and inner layers 120, 130 spaced apart by a circumferential cavity. In addition, the tubular body 110 includes end regions 114 that have a continuous wall between the outer and inner surfaces of the tubular body 110.

In an exemplary embodiment, the tubular body 110 may be formed by a sequential vapor deposition process, e.g., by first depositing material for an inner layer 130, applying a temporary middle layer or mask (not shown) over the inner layer 130, and then depositing additional material for an outer layer 120 over the middle layer. The middle layer may then be removed, e.g., by heating dissolution, and the like, leaving the outer and inner layers 120, 130 integrally formed adjacent one another.

Thus, the central region 112 may include outer and inner layers 120, 130 that are spaced apart or contact one another, yet are fixed relative to one another at the end portions 114. Struts or other elements (not shown) may be formed in the outer and inner layers 120, 130, e.g., opposite helical struts (not shown), similar to other embodiments herein. Simultaneously or sequentially, struts or other elements (not shown) may be formed in the end regions 114 to provide anchoring portions, also similar to other embodiments herein. If desired, flexible fixation points may be deposited or otherwise formed at discrete locations of the central region 112, e.g., coupling adjacent struts of the outer and inner layers 120, 130 together, as described elsewhere herein. Thus, a multilayer stent may be formed from a single tubular body instead of from multiple tubular bodies or flat sheets, which may be further processed and/or used, similar to other embodiments herein.

Figure 9A:
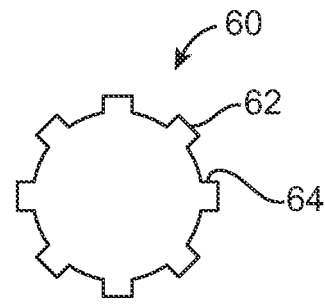
FIGS. 9A-9D are cross-sectional views of a cylindrical core or preform showing an exemplary method for forming a stent structure.
Figure 9B:
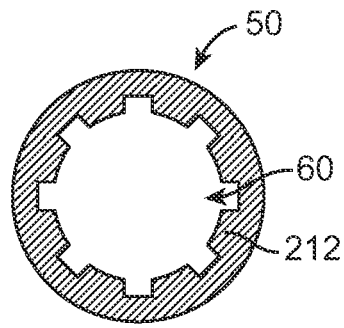
Figure 9C:
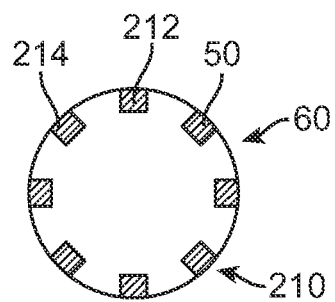
Figure 9D:
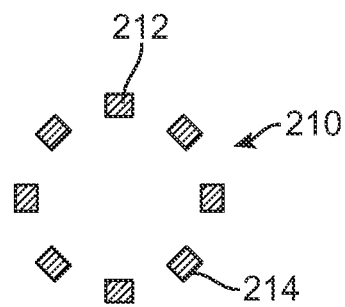
Figure 10:
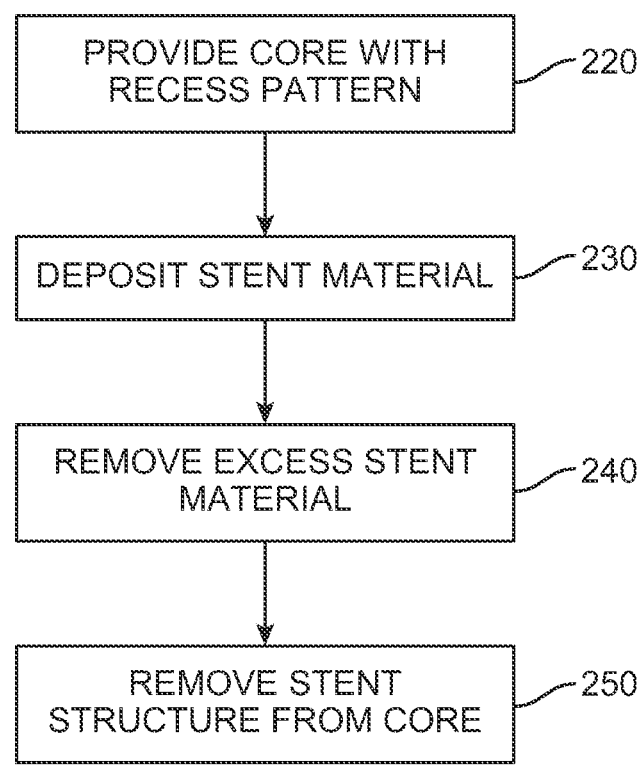
FIG. 10 is a flowchart showing an exemplary method for forming a stent structure, such as that shown in FIGS. 9A-9D.

Turning to FIGS. 9A-9D, in another embodiment, a stent structure 210 is shown being formed by deposition of stent material 50 onto a core or preform structure 60, e.g., using a method such as that shown in FIG. 10. The resulting stent structure 210 may be used for one or both of the outer and inner layers of a multi-layer stent (not shown), such as those described elsewhere herein, or for a single layer stent. In an exemplary embodiment, two or more stent structures may be formed using the method of FIGS. 9A-9D and 10, and the multiple stent structures may be attached together to provide a multi-layer stent, e.g., using methods similar to other embodiments herein.

Initially, at step 220 in FIG. 10, and as shown in FIG. 9A, a core 60 may be provided that includes a cylindrical outer surface 62 including a pattern of recesses 64 therein corresponding to a desired mesh pattern for a stent structure. The length of the core 60 may be substantially longer than the desired length of the stent structure 210, e.g., such that the recess pattern may terminate before ends of the core 60. Generally, the recesses 64 may provide a negative pattern for an arrangement of struts for the stent structure 210, where the outer surface 62 of the core 60 corresponds to the open spaces between the struts 212 of the resulting stent structure 210, and the recesses 64 have widths, depths, shapes, and/or other dimensions corresponding to those of the struts 212 to be formed (as shown in FIGS. 9C and 9D). For example, the recesses 64 may have three orthogonal walls defining substantially rectangular shapes to result in substantially rectangular struts of similar width and depth.

In an exemplary embodiment, the recesses 64 may define a plurality of helical channels (not shown) extending around the outer surface of the core 60, corresponding to the struts of the central portion 24, 34 of one of the stent layers 20, 30 shown in FIG. 3A or 3B. In this embodiment, optionally, the core 60 may also include recesses (not shown) corresponding to the struts of the anchoring portions 26, 36 of the stent layers 20, 30 shown in FIG. 3A or 3B, e.g., adjacent opposite ends of the core 60.

The core 60 may be formed, e.g., by molding, casting, machining, and the like, from materials capable of supporting stent material deposited thereon and sufficiently durable to endure the processing steps involved. In an exemplary embodiment, the core 60 may be provided with the pattern of recesses 64 formed therein when molded or cast. Alternatively, the recesses 64 may be created in the outer surface 62 after forming a uniform cylindrical core 60, e.g., by etching, machining, and the like.

In one embodiment, the core 60 may be formed from a polymer material that may have a softening or melting point substantially below temperatures that impact desired properties of the stent material, which may facilitate removal of the core 60 after processing, as described further below. Such cores may be relatively inexpensive to make, but may not be able to achieve extremely high tolerances of core dimensions, if desired.

Alternatively, the core 60 may be formed from ceramic, quartz, borosilicate glass, or similar materials, which may allow extreme precision in tolerances of the core dimensions. Such materials may also have coefficients of thermal expansion substantially lower than the stent material, which may facilitate removal of the core, as described further below. In additional alternatives, the core 60 may be formed from metal materials, e.g., which may be selectively etched to facilitate removal of the stent structure 210 after fabrication, or soluble casting materials, which may be dissolved to facilitate removal of the stent structure 210, as described further below.

At step 230, as shown in FIG. 9B, stent material 50 may be deposited onto the outer surface 62 of the core 60 to substantially fill the recesses 64. In an exemplary embodiment, the stent material, e.g., Nitinol or other metals, may be deposited onto the core 60, e.g., by sputtering, such as physical vapor deposition (PVD), electron-beam evaporative coating, laser ablation deposition, and the like. Exemplary methods that may be used are disclosed in U.S. Pat. No. 7,335,426, the entire disclosure of which is expressly incorporated by reference herein.

Figure 9E:
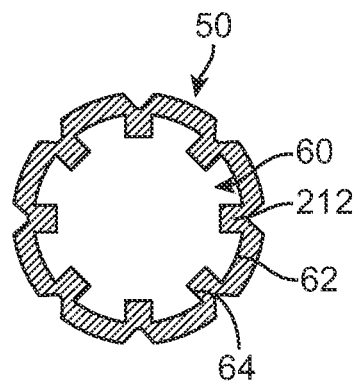
FIGS. 9E and 9F are cross-sectional views of alternative embodiments of methods for depositing stent material onto a preform.
Figure 9F:
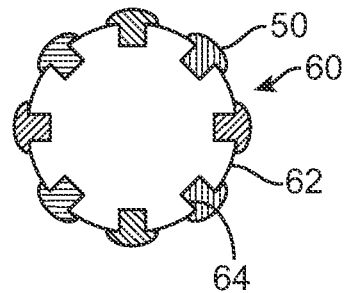

As shown in FIG. 9B, the stent material 50 may be deposited to a thickness that at least slightly overfills the recesses 64 in the outer surface 62, e.g., such that the stent material 50 defines a substantially uniform outer diameter greater than the preform 60. Alternatively, as turning to FIG. 9E, the stent material 50 may be deposited over the entire outer surface 62 of the preform 60 that does not define a substantially uniform outer diameter. For example, as shown in FIG. 9E, a substantially uniform thickness of stent material 50 may be deposited that is greater than the depths of the recesses 64 such that the deposited stent material has an undulated outer surface. In another alternative, shown in FIG. 9F, stent material 50 may be deposited to slightly overfill the recesses 64 without covering the entire outer surface 62 of the preform 60, e.g., by laser metal deposition or other methods.

As shown, a single layer of stent material 50 is deposited onto the core 60. In an alternative embodiment, multiple layers of stent material (not shown) may be deposited, if desired. For example, a first stent material may be deposited to partially fill the recesses 64, and then a second stent material may be deposited to overfill the recesses 64. Optionally, more than two layers may be deposited, as desired.

At step 240, as shown in FIG. 9C, excess stent material may be removed from the outer surface 62 of the core 60 to provide a desired outer surface 214 for the stent structure 210. For example, the core 60 may include countersunk centers (not shown), and the core 60 with deposited stent material 50 may be ground between centers to provide the desired outer surface 214. Alternatively, the core 60 may be ground using centerless grinding, if desired. In a further alternative, excess stent material may be removed using other processes, such as wire or other electrical discharge machining (EDM), machining, abrasive blasting, and the like.

As shown in FIG. 9C, the stent material 50 may be ground flush with the outer surface 62 of the core 60. Thus, the depth of the recesses 64 may determine the thickness of the struts 212 of the resulting stent structure 210. As shown in FIGS. 9A-9D, the recesses 64 may have substantially uniform depths. In this embodiment, the resulting struts 212 may have substantially uniform thicknesses throughout the stent structure 210.

Optionally, if desired, the depth of the recesses 64 may be varied at desired locations of the pattern, thereby resulting in the struts 212 having different thicknesses corresponding to the respective recess depths. In this manner, the mechanical properties of the struts 212 and corresponding regions of the stent structure 210 may be varied, if desired, e.g., to enhance flexibility at thinner regions and/or increase rigidity at thicker regions.

Returning to FIG. 10, at step 250, the stent structure 210 may be removed from the core 60, e.g., as shown in FIG. 9D. For example, if the core 60 is formed from a polymer material, the assembly may be heated to a temperature sufficient to at least partially soften or melt the core 60, e.g., without substantially impacting the properties and/or configuration of the stent structure 210. In one embodiment, the core 60 may simply be melted sufficiently to flow away from the stent structure 210. Alternatively, the core 60 may only be softened and then a tensile or other force may be applied, e.g., by pulling opposite ends of the core 60, to stretch the core 60, thereby causing the outer diameter of the core 60 to shrink and cause the regions of the core 60 between the struts 212 of the stent structure 210 to separate inwardly from the struts 212.

Alternatively, if the core 60 is formed from a low thermal expansion material, e.g., ceramic or glass, the core 60 and stent structure 210 may be heated sufficiently to cause greater expansion of the stent structure 210 than the core 60, such that the struts 212 expand out of the recesses 64. The core 60 may then be slid axially outer of the stent structure 210. It may also be possible to flex the stent structure 210 out of the recesses 64 of the core 60, e.g., within the elastic limits of the stent material, alone or in combination with any of these techniques. If the core 60 is not impacted by the processing and removal of the stent structure 210, the core 60 may be reused to make additional stent structures, if desired.

Alternatively, if the core 60 is formed from a soluble material, an appropriate solvent (that won't dissolve the stent material) may be applied, e.g., by dipping, pouring, and the like, until the core 60 is entirely dissolved or sufficiently dissolved to allow the remaining core material to be removed from within the stent structure 210. In a further alternative, at least the regions of the core 60 between the struts 212 may be removed, e.g., by dissolving, etching, and the like, e.g., if the core 60 is formed from different materials than the stent material and appropriate may be used to remove the core material without impacting the stent structure 210.

The resulting stent structure 210 may then be further processed as desired to provide a finished stent. For example, the stent structure 210 may be heat treated, may have one or more coatings applied thereto, and the like, similar to other embodiments herein. Optionally, the stent structure 210 may be coated before being removed from the core 60. For example, after removing excess stent material at step 240, one or more coatings may be applied to the stent structure 210. With the struts 212 still within the recesses 64, as shown in FIG. 9C, the coating(s) may be applied only to the outer surface 214 of the stent structure 210 and not to side and/or inner surfaces of the struts 212. Such coatings may be applied over the entire outer surface 214 or selectively over discrete regions of the outer surface 214. Exemplary coatings may include therapeutic materials, radiopaque materials, and the like.

In another embodiment, one or more films (not shown) may be applied to the outer surface 214 of the stent structure 210, e.g., before removing the struts 212 from the recesses 64. For example, a relatively thin film, e.g., a Nitinol film having a thickness between about two and twenty five microns (2-25 μm), may be applied to the stent structure 210, e.g., by vapor deposition, and the like. Thereafter, before or after removing the stent structure from the core, the stent structure 210 and/or thin film cover may be laser ablated to create a desired pattern in the thin film cover, e.g., a grid. The stent structure 210 may then be separated from the core 60, leaving a stent scaffold with an intimately attached thin film cover with a desired pattern, e.g., that allows expansion or compression.

Figure 11A:
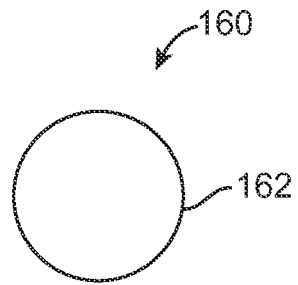
FIGS. 11A-11L are cross-sectional views of a cylindrical core or preform showing another exemplary method for forming a stent structure.
Figure 11B:
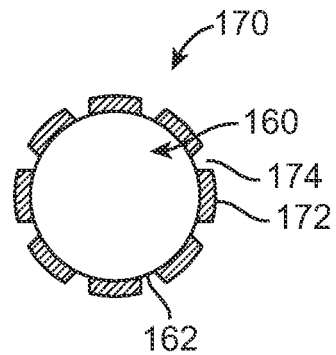
Figure 11C:
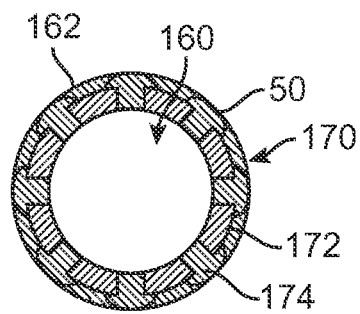
Figure 11D:
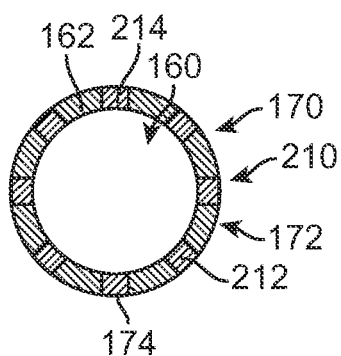
Figure 11E:
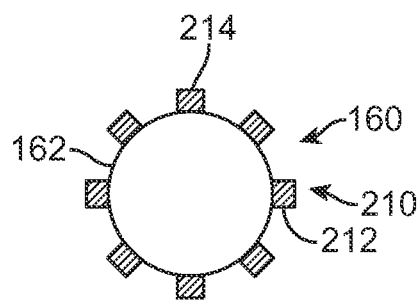
Figure 11F:
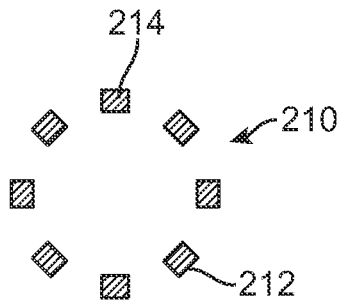
Figure 12:
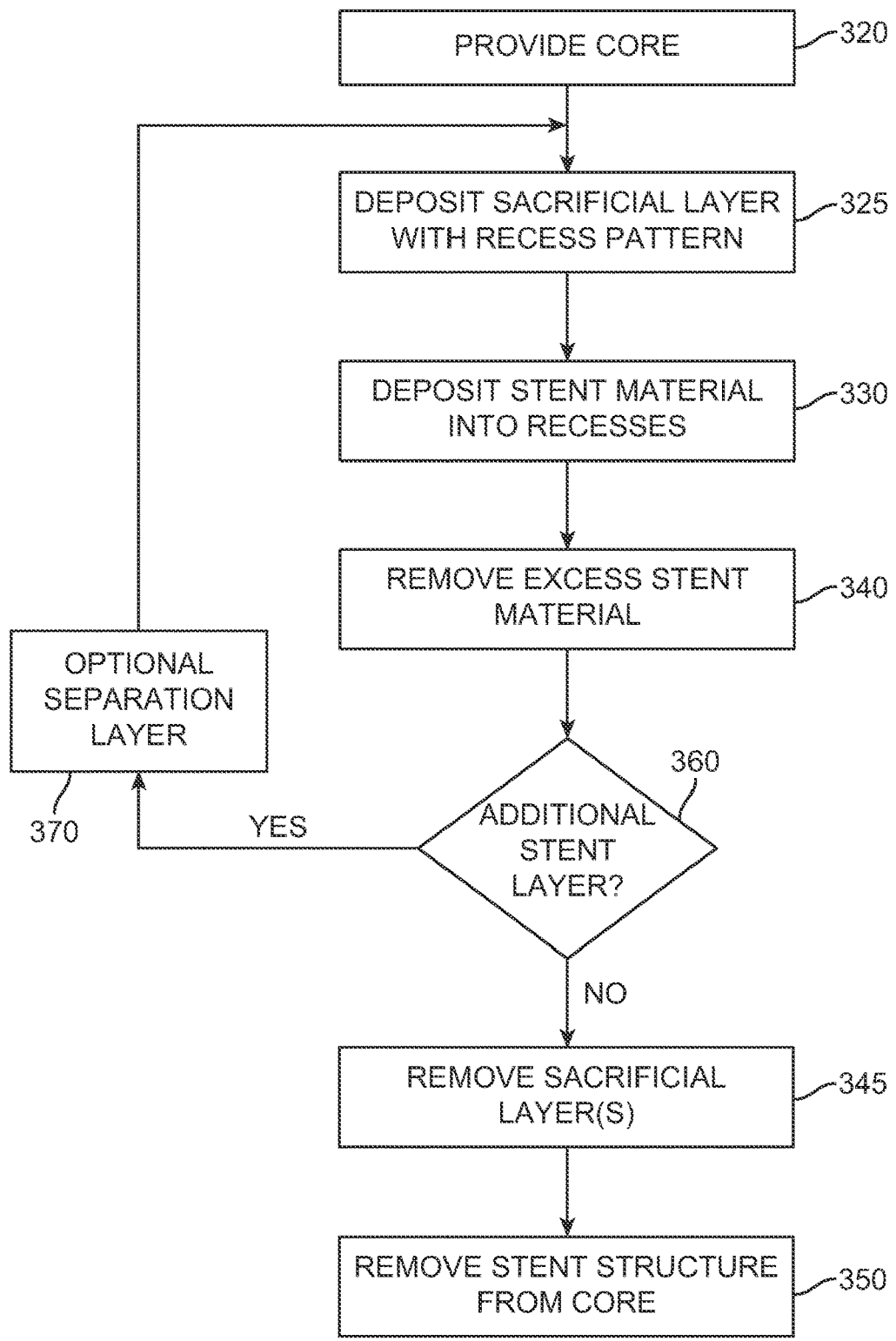
FIG. 12 is a flowchart showing an exemplary method for forming a stent structure, such as that shown in FIGS. 11A-11L.

Turning to FIGS. 11A-11F, in another embodiment, a stent structure 310 (similar to any of the other embodiments herein) may be formed by deposition of stent material 50 onto a core or preform structure 160 having one or more sacrificial layers or masks 170 formed thereon, e.g., using a method such as that shown in FIG. 12. Initially, at step 320 in FIG. 12, a core 160 may be provided, e.g., having a substantially uniform outer surface 162 (e.g., without recesses), as shown in FIG. 11A. In exemplary embodiments, the core 160 may be formed from durable, e.g., reusable, materials, such as metal, ceramic, quartz, or glass.

At step 325, one or more sacrificial layers 170 may be applied to the outer surface 162 of the core 160. In exemplary embodiments, the sacrificial layer(s) 170 may be applied by one of photolithography, printing, and molding on the outer surface 162 of the core 160. For example, a discontinuous sacrificial layer 170 may be deposited onto the outer surface 162 of the core 160 to create a pattern of recesses 174 between regions of the sacrificial layer 174, with the recesses 174 corresponding to a desired mesh pattern for a stent structure, similar to the previous embodiments. The sacrificial layer 170 may have a substantially uniform thickness on the outer surface 162, e.g., such that the recesses 174 have substantially uniform depths and the outer surface 172 of the sacrificial layer 170 defines a substantially uniform diameter. Alternatively, if desired, the thickness may be varied, e.g., to provide different depth recesses, and consequently variable thickness struts in a stent structure (not shown).

At step 330, stent material is deposited to substantially fill the recesses 174, thereby creating a plurality of struts 212 within the recesses 174 defining the desired mesh pattern, as shown in FIG. 11C. In an exemplary embodiment, one or more layers of stent material, e.g., Nitinol or other metals, may be deposited onto the core 160, e.g., by sputtering, to a thickness that at least slightly overfills the recesses 174 and/or covers the outer surface 174 of the sacrificial layer 170, e.g., similar to other embodiments herein.

At step 340, excess stent material may be removed, e.g., by grinding, similar to other embodiments herein. For example, as shown in FIG. 11D, the stent material 50 may be ground flush with the outer surface 172 of the core sacrificial layer 170. Thus, the depth of the recesses 174 may determine the thickness of the struts 212 of the resulting stent structure 210.

If a single layer stent structure 210 is being created, at decision point 360 in FIG. 12 (additional layer is "no"), steps 345 and 350 may be performed next. Alternatively, as described further below, if one or more additional layers of stent material are to be deposited, one or more steps may be repeated (additional layer is "yes"). For example, for a single layer stent structure 210, at step 350, the sacrificial layer 170 may be removed from the core 160, leaving the stent material on the outer surface 162 of the core 160, as shown in FIG. 11E. In exemplary embodiments, the sacrificial layer 170 may be removed by etching, dissolving, and the like.

Optionally, if desired, one or more coatings (not shown) may be applied to the stent material, similar to other embodiments herein. For example, in one embodiment, after the excess stent material is ground or otherwise removed to define the desired outer surface 214 of the stent structure 210 but before removing the sacrificial layer 170, a coating may be applied. Because the struts 212 of the stent 210 remain within the recesses 174, as shown in FIG. 11D, in this embodiment, the coating is only applied to the outer surfaces 214 of the stent structure 214. In an alternative embodiment, the sacrificial layer 170 may be removed from the core 160 before the coating is applied, e.g., as shown in FIG. 11E. In this embodiment, because the struts 212 are partially exposed, the coating may be applied to both the outer surface 214 and side surfaces of the stent structure 210, without applying the coating to the inner surface of the stent structure 210.

Returning to FIG. 12, at step 350, after removing the sacrificial layer 170 (and/or after applying any desired coatings), the stent structure 210 may be removed from the core 160. Given that the sacrificial layer 170 has been removed, the stent structure 210 may simply be slid over the outer surface 162 from around the core 160. Optionally, the stent structure 210 may be processed further and/or combined with one or more additional stent structures (not shown), similar to other embodiments herein.

Optionally, it may be possible to form a multi-layered stent (not shown) on a core, e.g., onto a first stent structure 210 formed on the core 160 shown in FIG. 11D. For example, with reference to FIG. 12, if one or more additional layers are to be deposited at decision point 360, steps 325 to 340 may be repeated one or more times.

Figure 11G:
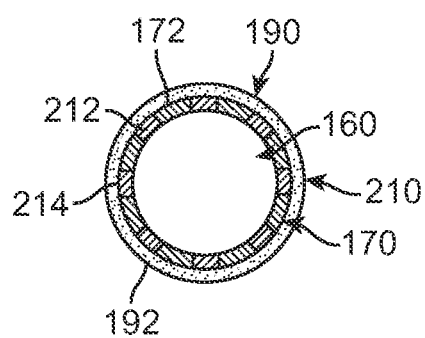
Figure 11H:
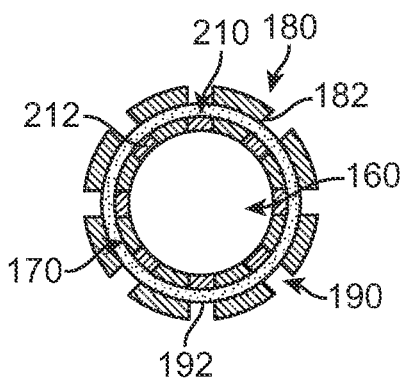

In particular, as shown in FIGS. 11G-11L, after removing the excess stent material at step 340 (as shown in FIG. 11D), a second sacrificial layer 180 may be deposited over the first sacrificial layer 170 and the first stent structure 210, e.g., to create a pattern of second recesses 182 between regions of the second sacrificial layer 180 corresponding to a desired mesh pattern for a second stent structure 310, e.g., as shown in FIG. 11H. Optionally, at step 370 in FIG. 12, a sacrificial separation layer 190 may be deposited over at least a portion of the first sacrificial layer 170 and the stent structure 210 before depositing the second sacrificial layer 180, e.g., as shown in FIG. 11G.

In an exemplary embodiment, a substantially uniform thickness layer of sacrificial material may be deposited to provide a substantially uniform outer surface 192 to receive the second sacrificial layer 180 and second stent structure 310. The separation layer 190 may be formed from the same or similar materials to the first and second sacrificial layers 170, 180, e.g., such that all of the sacrificial layers may be removed at the same time. Alternatively, the separation layer 190 may be formed from different materials than the first and/or second sacrificial layers 170, 180.

Such a separation layer 190 may ensure that at least some of the struts of the resulting inner and outer stent structures are independently movable relative to one another, similar to other embodiments herein. For example, for the multi-layer stent 10 shown in FIG. 1, the separation layer 190 may be deposited only in the region corresponding to the central portion 12, e.g., to allow the outer and inner struts 22, 32 to remain independently movable from one another. For example, if the separation layer 190 is relatively thinner than the first and second sacrificial layers 170, 180, the resulting struts 212, 312 may remain in close, e.g., sliding, proximity with one another while remaining independent from one another. With no separation layer deposited in the region corresponding to the anchoring portions 14, the stent material for the outer struts 28 may be deposited directly onto the stent material for the inner struts 38.

Figure 11I:
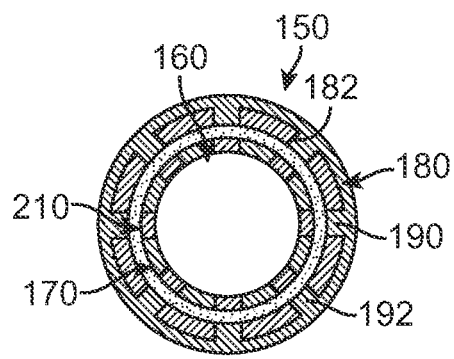
Figure 11J:
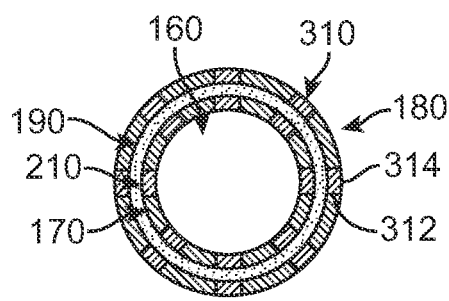

Returning to FIG. 12, once the second sacrificial layer 180 is deposited (at repeated step 325), stent material 150 may be deposited to substantially fill the second recesses 182 (at repeated step 330), thereby creating a plurality of second struts 312, as shown in FIG. 11I. Excess stent material may be ground or otherwise removed from the second struts 312 (at repeated step 340) to define a second stent structure 310, as shown in FIG. 11J.

Figure 11K:
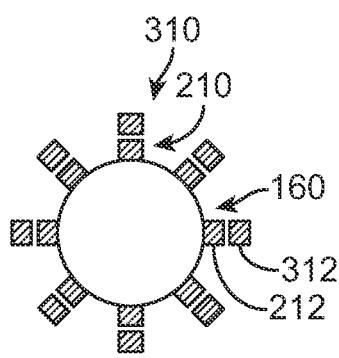
Figure 11L:
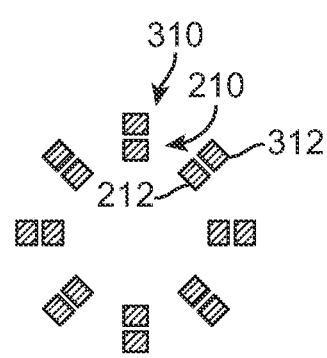

After one or more additional layers have been deposited, the sacrificial layers may be removed at step 345 in FIG. 12, e.g., similar to other embodiments herein, leaving multiple stent layers on the outer surface of the core. For example, as shown in FIG. 11K, after depositing first and second stent structures 210, 310, the first, second, and sacrificial layers 170, 180, 190 may be removed, e.g., etching, dissolving, and the like. The resulting stent structures 210, 310 may be removed from the core 160 at step 350 in FIG. 12, to provide a two layer stent structure, as shown in FIG. 11L, and processed further, as desired to provide a multi-layered stent.

In other embodiments, it may be possible to create a positive image of a stent on the outer surface of a core, and then remove the core. The interior of the preform may then be processed, e.g., by grinding, machining, EDM, and the like, to yield a finished stent. In yet another embodiment, a stent structure may be directly formed on an outer surface of a core, e.g., by laser direct metal deposition where wire or powder metal is fused via laser as an additive process to create the stent structure.

It will be appreciated that elements or components shown with any embodiment herein are exemplary for the specific embodiment and may be used on or in combination with other embodiments disclosed herein. While the disclosed and described embodiments are susceptible to various modifications, and alternative forms, specific examples thereof have been shown in the drawings and are herein described in detail. It should be understood, however, that the disclosed inventions are not to be limited to the particular forms or methods disclosed, but to the contrary, cover all modifications, equivalents and alternatives falling within the scope of the appended claims.

What is claimed is:

1. A multilayer stent configured for implantation in a body lumen, comprising:
 a tubular outer layer comprising a first plurality of struts defining an outer layer mesh pattern extending between first and second ends of the outer layer, a proximal anchoring portion extending proximally from the first end of the outer layer, and a distal anchoring portion extending distally from the second end of the outer layer, the outer layer having a central portion consisting only of struts wound in a substantially helical configuration and arranged parallel to each other; and
 a tubular inner layer comprising a second plurality of struts defining an inner layer mesh pattern extending between first and second ends of the inner layer, a proximal anchoring portion extending proximally from the first end of the inner layer, and a distal anchoring portion extending distally from the second end of the inner layer, the inner layer having a central portion consisting only of struts wound in a substantially helical configuration and arranged parallel to each other, the inner-layer at least partially disposed within the outer layer,
 wherein at least a portion of the inner layer is attached to the outer layer at a plurality of discrete fixation points near transitions between the central portion and the proximal anchoring portion and between the central portion and the distal anchoring portion and the inner layer and outer layer are not attached to each other elsewhere within the central portion, wherein the respective proximal anchoring portions and distal anchoring portions of the outer layer and inner layer comprise respective zigzag struts such that the zigzag struts of the proximal anchoring portion of the outer layer overlie and are aligned over respective zigzag struts of the proximal anchoring portion of the inner layer, and zigzag struts of the distal anchoring portion of the outer layer overlie and are aligned over respective zigzag struts of the distal anchoring portion of the inner layer, and wherein the struts of the central portion of the outer layer are not aligned with, and are movable relative to, the struts of the central portion of the inner layer.

2. The multilayer stent of claim 1, wherein the inner layer and outer layer are formed from a single piece of material.

3. The multilayer stent of claim 1, wherein the inner layer and outer layer are formed from separate pieces of material, and are attached to one another at the plurality of discrete fixation points.

4. The multilayer stent of claim 1, wherein the outer layer mesh pattern and the inner layer mesh pattern together define a porosity of the stent.

5. The multilayer stent of claim 1, the stent defining a stent axis, wherein one of the first plurality of struts and second plurality of struts comprises helical struts extending in a clockwise direction relative to the stent axis, and the other of the first plurality of struts and second plurality of struts comprises helical struts extending in a counterclockwise direction relative to the stent axis, such that struts of the first plurality cross at an angle over struts of the second plurality.

6. The multilayer stent of claim 1,
wherein one or more zigzag struts of the proximal anchoring portion of the inner layer are attached to, or integrally formed with, one or more zigzag struts of the proximal anchoring portions of the outer layer, and
wherein one or more zigzag struts of the distal anchoring portion of the inner layer are attached to, or integrally formed with, one or more zigzag struts of the distal anchoring portion of the outer layer.

7. The multilayer stent of claim 6, wherein the respective proximal and distal anchoring portions of the inner and outer layers are all formed from a single layer of material.

8. The multilayer stent of claim 6, the inner layer and outer layer being formed from separate pieces of material, and wherein one or more zigzag struts of the proximal anchoring portion of the inner layer are attached to respective one or more zigzag struts of the proximal anchoring portion of the outer layer at a first plurality of fixation points, and one or more zigzag struts of the distal anchoring portion of the inner layer are attached to respective one or more zigzag struts of the distal anchoring portion of the outer layer at a second plurality of fixation points.

9. The multilayer stent of claim 1,
the stent having a delivery configuration sized for introduction into a body lumen, and an expanded configuration for implantation in the body lumen,
wherein the stent is biased to the expanded configuration, and
wherein the outer layer mesh pattern and inner layer mesh pattern together define a porosity through a sidewall of the stent that includes an open area between about fifty and ninety percent (50-90%) in the expanded configuration.

10. The multilayer stent of claim 1, further comprising a plurality of flexible fixation points coupling struts of the first plurality to adjacent struts of the second plurality at discrete locations.

11. The multilayer stent of claim 1, further comprising one or more features formed on at least one of an outer surface of the inner layer and an inner surface of the outer layer to reduce sliding motion of struts of the first plurality relative to struts of the second plurality.

12. The multilayer stent of claim 1, wherein one or more zigzag struts of the proximal anchoring portion of the inner layer are attached to one or more zigzag struts of the proximal anchoring portion of the outer layer at proximal anchoring portion fixation points, and
wherein one or more zigzag struts of the distal anchoring portion of the inner layer are attached to, or integrally formed with, one or more zigzag struts of the distal anchoring portion of the outer layer at distal anchoring portion fixation points.

13. The multilayer stent of claim 12, wherein the proximal anchoring portion fixation points are located only on every other tip of the zigzag struts of the inner layer and outer layer of proximal anchoring portion and the distal anchoring portion fixation points are located only on every other tip of the zigzag struts of inner layer and outer layer of the distal anchoring portion.

* * * * *